(12) United States Patent
Virmani

(10) Patent No.: US 9,020,578 B2
(45) Date of Patent: Apr. 28, 2015

(54) COLONOGRAPHY

(75) Inventor: Sunny Virmani, Twinsburg, OH (US)

(73) Assignee: Koninklijke Philips N.V., Eindhoven (NL)

( * ) Notice: Subject to any disclaimer, the term of this patent is extended or adjusted under 35 U.S.C. 154(b) by 168 days.

(21) Appl. No.: 13/379,757

(22) PCT Filed: Jun. 14, 2010

(86) PCT No.: PCT/IB2010/052653
§ 371 (c)(1),
(2), (4) Date: Dec. 21, 2011

(87) PCT Pub. No.: WO2011/001313
PCT Pub. Date: Jan. 6, 2011

(65) Prior Publication Data
US 2012/0101360 A1  Apr. 26, 2012

Related U.S. Application Data

(60) Provisional application No. 61/222,151, filed on Jul. 1, 2009, provisional application No. 61/237,052, filed on Aug. 26, 2009.

(51) Int. Cl.
*A61B 5/05* (2006.01)
*A61B 6/00* (2006.01)
*A61B 6/03* (2006.01)
*A61M 13/00* (2006.01)
*G06F 19/00* (2011.01)

(52) U.S. Cl.
CPC ............... *A61B 6/466* (2013.01); *A61B 6/032* (2013.01); *A61B 6/50* (2013.01); *A61M 13/003* (2013.01); *G06F 19/321* (2013.01); *G06F 19/325* (2013.01); *G06F 19/3406* (2013.01)

(58) Field of Classification Search
CPC ..... A61M 13/003; A61M 5/00; A61M 5/007; A61M 5/14; A61B 5/002; A61B 1/015; A61B 6/54; A61B 6/466; A61B 6/032; A61B 6/50; G06F 19/321; G06F 19/325; G06F 19/3406
USPC ................................. 600/118–158, 407–436
See application file for complete search history.

(56) References Cited

U.S. PATENT DOCUMENTS

| 5,160,724 | A | * | 11/1992 | Tonariya et al. | 424/9.411 |
|---|---|---|---|---|---|
| 5,385,156 | A | * | 1/1995 | Oliva | 128/898 |
| 5,518,711 | A | * | 5/1996 | Tonariya et al. | 424/9.411 |
| 6,850,792 | B2 | | 2/2005 | Ohishi | |
| 7,940,967 | B2 | * | 5/2011 | Ozaki et al. | 382/128 |
| 2005/0203389 | A1 | | 9/2005 | Williams | |
| 2006/0047184 | A1 | * | 3/2006 | Banik et al. | 600/156 |
| 2006/0100500 | A1 | * | 5/2006 | Williams, Jr. | 600/410 |
| 2006/0242096 | A1 | * | 10/2006 | Ozaki et al. | 706/23 |
| 2006/0287645 | A1 | * | 12/2006 | Tashiro et al. | 606/1 |

(Continued)

FOREIGN PATENT DOCUMENTS

| JP | 01164353 A | 6/1989 |
|---|---|---|
| JP | 02224647 A | 9/1990 |

(Continued)

*Primary Examiner* — Sanjay Cattungal

(57) ABSTRACT

A system includes an insufflator (120) and an imaging system (100). The imaging system (100) includes a console (118). The console (118) and the insufflator (120) are in communication. The console (118) controls operation of the insufflator (120).

26 Claims, 3 Drawing Sheets

(56) References Cited

U.S. PATENT DOCUMENTS

2007/0078328 A1* 4/2007 Ozaki et al. .................. 600/407
2012/0101334 A1* 4/2012 Banik et al. .................. 600/118
2012/0130304 A1* 5/2012 Barish et al. .................... 604/24
2013/0102882 A1* 4/2013 Williams, Jr. ................ 600/415

FOREIGN PATENT DOCUMENTS

| JP | 03126466 A | 5/1991 |
|----|------------|--------|
| WO | 2009064718 A1 | 5/2009 |

* cited by examiner

COLONOGRAPHY

CROSS REFERENCE TO RELATED APPLICATIONS

This application claims the benefit of U.S. provisional application Ser. No. 61/222,151 filed Jul. 1, 2009 and U.S. provisional application Ser. No. 61/237,052 filed Aug. 26, 2009, both of which are incorporated herein by reference.

The following generally relates to colonography, and is described with particular application to computed tomography (CT); however, it is also amenable to other imaging modalities.

CT colonography (or virtual colonoscopy) is an imaging procedure in which the colon is scanned. For a typical CT colonography, the patient is placed in a supine position on the exam table. The colon is then insufflated to inflate the colon for scanning and viewing purposes. For this, the patient rolls either to the left or right side, and the colon is insufflated with carbon dioxide up to a predetermined volume and pressure. The patient then rolls to the other side, and the colon is further insufflated to a predetermined amount and pressure of carbon dioxide. The patient then rolls back to the supine position, and the colon is scanned. In some instances, the above may also repeated for the prone position.

The resulting imaging data provides cross-sectional data along the length of the colon and can be used to generate three-dimensional imaging data. The imaging data can be displayed and scrolled through as individual cross-sectional images and/or used to generate a three dimensional cine or movie, which allows a user to simulate moving through the patient's actual colon as if performing conventional colonoscopy. Such data may facilitate screening for colon cancer and/or other colon abnormalities of the colon.

For a conventional CT colonography, the user (radiological technician or clinician) manually operates an insufflator to insufflate the colon. During insufflation, the user monitors the volume and the pressure of carbon dioxide being insufflated into the colon. This allows the user to determine when a sufficient amount of carbon dioxide has been insufflated for a particular side, when the patient should roll to the other side, and when the predetermined amounted of carbon dioxide has been reached. Once the colon is suitably insufflated, the user exits the exam room and initiates scanning.

Unfortunately, this approach requires the user to be at the patient's side in the exam room during insufflation. In addition, the user is required to monitor the amount of carbon dioxide insufflated and manually start and stop insufflation. Moreover, the user may not know whether the colon is still suitably insufflated at the time of scanning, as carbon dioxide can leak out prior to scanning.

Aspects of the present application address the above-referenced matters and others.

According to one aspect, a system includes an insufflator and an imaging system. The imaging system includes a console. The console and the insufflator are in communication. The console controls operation of the insufflator.

In another embodiment, a method includes controlling an insufflator during a colonography imaging procedure in which the insufflator is used to insufflate the colon of a patient via a console of an imaging system used to perform the colonography imaging procedure.

In another embodiment, a method includes validating, via a processor, a colonography imaging procedure based on insufflation information received from an insufflator controlled by an imaging system and insufflation parameters from a corresponding imaging protocol.

In another embodiment, a method includes generating, via a processor, a colonography imaging protocol, including one or more insufflation parameters for an insufflator controlled by an imaging system executing the imaging protocol, based on one or more insufflation parameters of at least one previously performed colonography imaging procedure.

The invention may take form in various components and arrangements of components, and in various steps and arrangements of steps. The drawings are only for purposes of illustrating the preferred embodiments and are not to be construed as limiting the invention.

Figure 1:
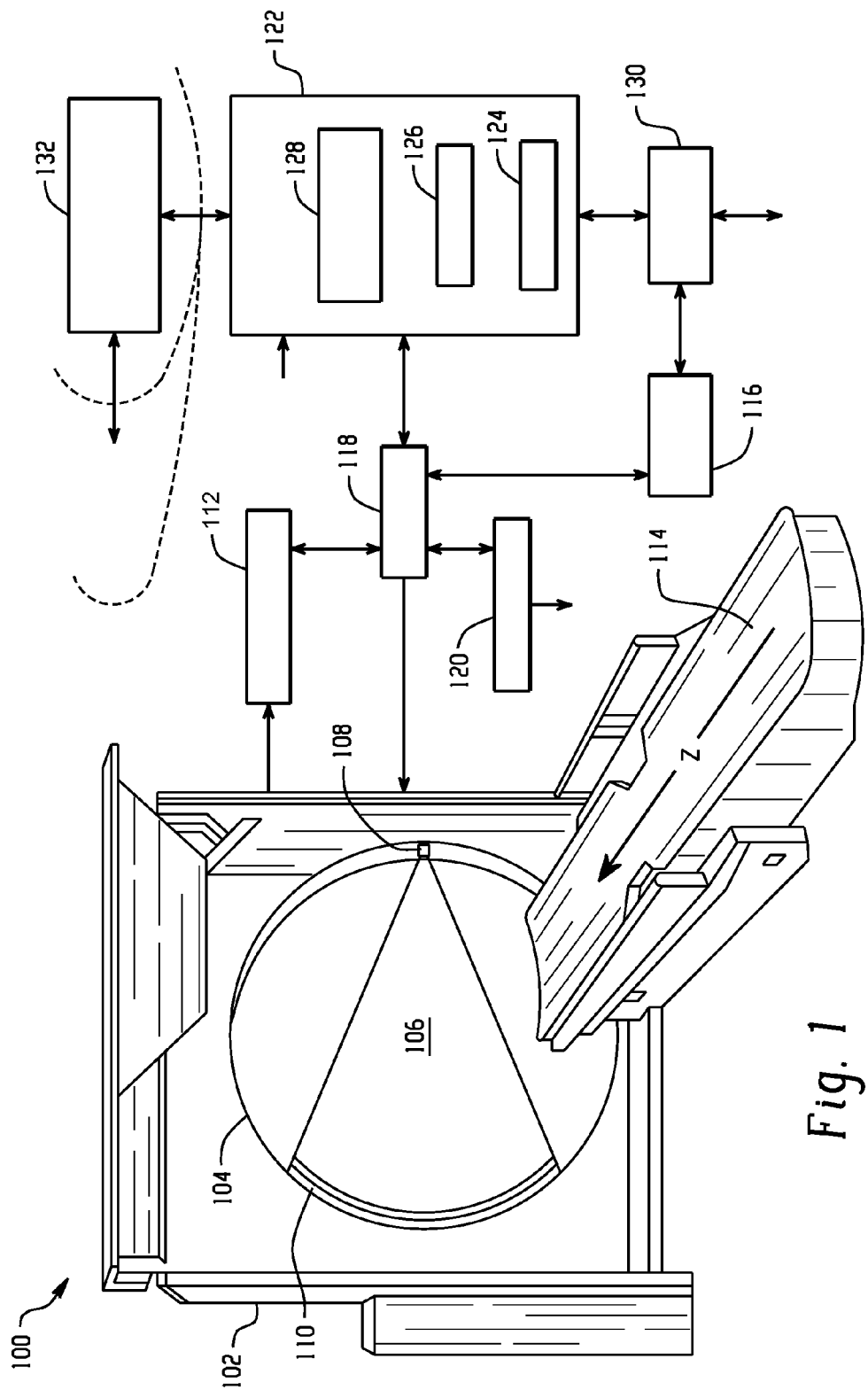
FIG. 1 illustrates an imaging system in connection with an insufflator.

Initially referring to FIG. 1, an imaging system 100, such as a CT scanner, includes a stationary gantry 102 and a rotating gantry 104, which is rotatably supported by the stationary gantry 102 and rotates around an examination region 106 about a z-axis. A radiation source 108, such as an x-ray tube, is supported by the rotating gantry 104 and emits radiation that traverses the examination region 106. A radiation sensitive detector array 110 subtends an angular arc opposite the radiation source 108 across the examination region 106, detects radiation traversing the examination region 106, and generates projection data or a signal indicative thereof. A reconstructor 112 reconstructs the signal and generates volumetric image data indicative thereof. A patient support 114, such as a couch, supports an object or subject in the examination region 106.

A protocol bank 116 stores imaging protocols used by the system 100, including at least one colonography imaging protocol. A general-purpose computing system serves as an operator console 118. The console 118 includes a processor that executes computer executable instructions stored on computer readable memory. The instructions allow the operator to control operation of the system 100 such as selecting an imaging protocol (e.g., scout protocol, colonography imaging protocol, etc.) from the protocol bank 116, controlling auxiliary devices connected to the system 100 (e.g., an insufflator, an injector, an EKG monitors, etc.), initiating and terminating scanning, etc. The console 118 also includes a communications interface for communicating with one or more auxiliary devices, including receiving information from and/or sending information to the auxiliary device.

An insufflator 120 is used to inject a gas, such as carbon dioxide, air, or other gas suitable to be injected into a cavity of the patient, into the patient's colon to insufflate the colon for a colonography imaging procedure or other procedure. The insufflator 120 includes a user interface for manual programming various insufflation parameters of the insufflator 120 such as insufflation rate and volume, starting insufflation, monitoring insufflation, stopping insufflation, turning the insufflator on and off, etc. The insufflator 120 also includes a communications interface for communicating with one or more devices. In one embodiment, the insufflator 120 can receive control signals, insufflation parameters and/or other information from the console 118 and/or other apparatus via the communications interface.

In the illustrated embodiment, the console 118 and the insufflator 120 communicate with each other through their respective communications interfaces. Such communication may involve control of the insufflator 120 by the console 118, including starting and stopping the insufflator 120, setting one or more insufflation parameters of the insufflator 120 such as an insufflation rate, insufflation volume and insufflation pressure, pausing the insufflator, etc. Such communication may also includes the insufflator 120 sending feedback to the console 118, including information indicative of insufflation start time, insufflation stop time, insufflation pauses, an insufflation rate, an insufflation volume, an insufflation pressure, etc. In one instance, the console 118 processes feedback information, such as the insufflator volume and/or pressure, and prompts the operator to begin the scan based on the feedback insufflator volume and/or pressure.

A computing device 122 processes imaging data (projection and/or reconstructed image data) and insufflation information (e.g., rate, volume, start time, stop time, etc.). The illustrated computing device includes a correlator 124, a validator 126 and a presentation component 128.

The correlator 124 correlates imaging data and insufflation information. In one instance, the imaging data and the insufflation information are correlated based on time. By way of example, in one instance the correlator 124 correlates the imaging data and insufflation information based on time stamps included with the imaging data and insufflation information. In another instance, the correlator 124 correlates the imaging data and insufflation information based on a time of arrival of the imaging data and insufflation information at the console or the computing device 122, for example, where the imaging data and insufflation information are conveyed in real time. Various information can be obtained from the correlated data. For example, the time from insufflation (start and/or end) to scanning can be determined from this data. In another example, an insufflation volume at scan time can be determined. In another example, an estimated insufflation volume for particular imaging data (taking into account approximated gas leakage out of the colon over time) can be determined.

The validator 126 facilitates (post) validating an imaging procedure and/or procedure parameters, including the insufflation parameters and the scanning parameters. In this example, the computing device 122 includes a user interface allowing an operator to interact with the validator 126. The operator can provide information such as whether the colon was sufficiently insufflated based on the scout scan, based on the imaging data, based on the insufflation volume, based on insufflation pressure at the time of scanning, based on an estimated insufflation volume for particular imaging data, etc. The validator 126 can also automate validation by automatically validating actual values such as actual insufflation volume or pressure with the insufflation volume or pressure parameter defined in the imaging protocol.

The presentation component 128 presents the processed imaging data and the insufflation information, including correlation information and/or validation information. In one instance, the presentation component 128 presents the imaging data and the insufflation information in separate viewing regions of a display. In another instance, the presentation component 128 presents the imaging data and the insufflation information in a same viewing region, for example, superimposed or otherwise combined. In yet another instance, the imaging data and/or the insufflation information are included in a report, printed, conveyed to another device over a network, bus or the like, locally and/or remotely stored, etc.

The illustrated computing device 122 is shown separate from the system 100 and includes one or more processors for processing, correlating, validating and/or presenting data. In another embodiment, one or more of the components of the computing device 122 (the correlator 124, the validator 126, the presentation component 128, etc.) are part of the console 118 and executed by one or more processors thereof. In another embodiment, one or more of the components of the computing device 122 are part of one or more other devices, including distributed amongst a plurality of devices.

A protocol generator 130 includes a processor that executes computer readable instructions for facilitating generating imaging protocols based on the output of the computing device 122 and/or user input. The protocol generator 130 may use various machine-learning algorithms, Bayesian algorithms, neural networks, state vector machines, inference engines, explicitly and/or implicitly trained classifiers and/or other algorithms to generate imaging protocols based on the output of the computing device 122 and/or user input. Examples of such imaging protocols include follow up protocols, general protocols, patient specific protocols, and/or other imaging protocols and may include insufflator 120 parameters such as insufflation rate, volume, etc. and/or scanning parameters such as time from insufflation to scanning, etc. In one instance, for example, where an imaging procedure has been validated, the same imaging protocol is used for a follow up study of the patient. In another instance, for example, where the imaging procedure did not pass validation, the protocol generator 130 generates a new imaging protocol or a modified imaging protocol for the follow up study. Similar to the computing device 122, the protocol generator 130 can be separate from (as shown) or part of the console 118.

Imaging data, an imaging protocol, scanning parameters, and/or insufflation parameters can be conveyed to another computing system and/or storage system. In one instance, this includes packaging the information in a Digital Information Imaging and Communications in Medicine (DICOM) or other format and sending the packaged data to a Picture Archiving and Communication System (PACS), a Radiology Information System (RIS), a Hospital Information System (HIS), and/or other storage and/or archival system.

In another instance, this includes providing imaging data, an imaging protocol, scanning parameters and/or insufflation parameters to a web service such as a protocol storing and/or generating web service 132. The illustrated web service 132 stores such information and/or generates new and/or modified protocols, similar to the protocol generator 130. The web service 132 can be a subscription or otherwise based service that allows an authorized user to upload and/or download such information on a subscription basis, including flat fee, per use fee, or for free, based on a level of access of the user, which can be a single hospital, a network of hospitals, a contracted radiological or other group, etc.

Figure 2:
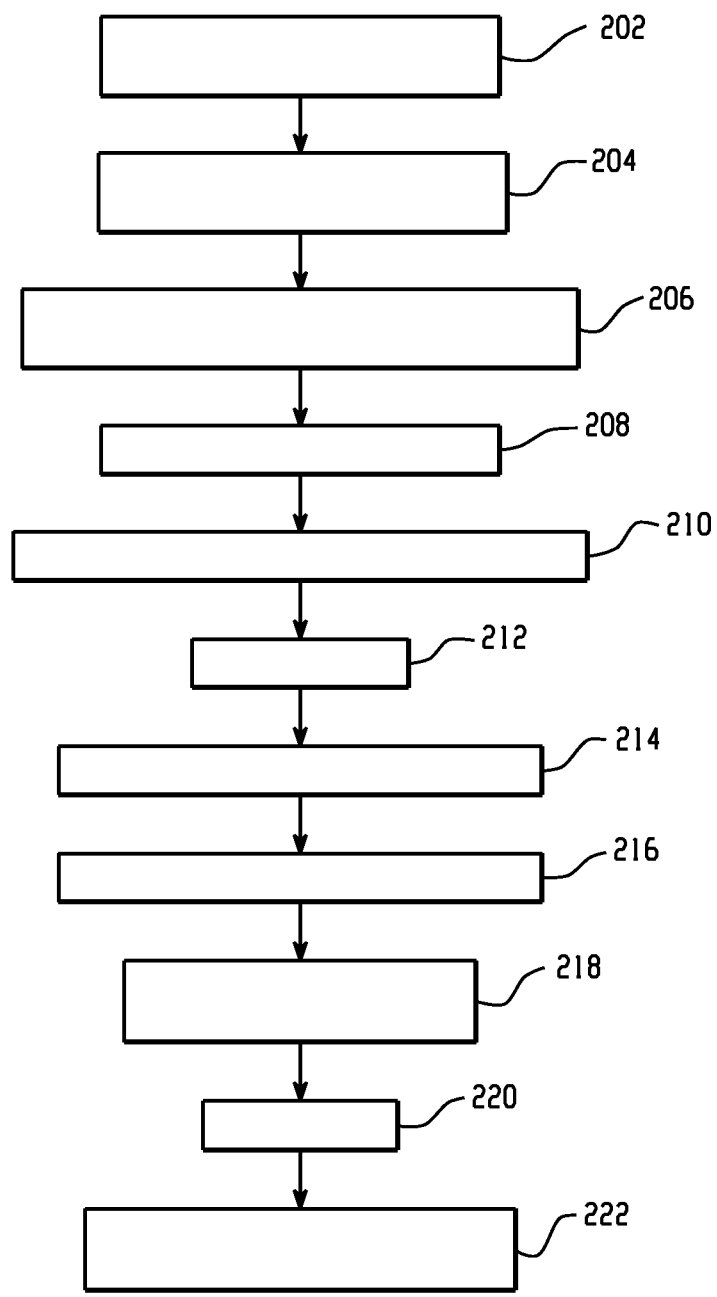
FIG. 2 illustrates a method for controlling an insufflator with a console of an imaging system during a colonography imaging procedure.

FIG. 2 illustrates a method for employing the console 118 to control the insufflator 120 for a colonography imaging procedure.

At 202, the insufflator 120 is interfaced with the system 100.

At 204, an operator interacts with a console application executing on the console 118 and selects a suitable imaging protocol employing the insufflator 120 such as a colonography imaging protocol. The operator may modify one or more of the parameters of the protocol, including at least one parameter of the system 100 and/or at least one parameter of the insufflator 120.

At 206, the selected protocol is loaded. This includes setting the scanning parameters and downloading insufflator parameters to the insufflator 120. Insufflator parameters include, but are not limited to, one or more of insufflation rate, insufflation volume, insufflation pressure etc.

At 208, the console application prompts the operator to have the patient lie on the support 114 (e.g., in the supine position) and insert an insufflation tube of the insufflator 120 in the colon of the patient. The operator provides an input to the console indicating that the tube has been inserted, once the tube is inserted.

At 210, the console application prompts the operator to have the patient roll onto their side (right or left). The operator provides an input to the console 118 indicating that the patient is on their side once the patient rolls to their side.

At 212, the console application, in response to an operator input indicating the procedure should begin, invokes the insufflator 120 to insufflate the colon based on the downloaded insufflation parameters.

At 214, the insufflator 120 provides insufflation feedback to the console 118, and the console application monitors the feedback. Such feedback may include insufflation rate, insufflation volume, insufflation pressure, elapsed time, etc. The console application may graphically and/or audibly present this information via a console display and/or speaker.

At 216, the console application pauses or stops the insufflator 120 in response to the insufflation volume reaching the downloaded insufflation volume parameter and/or the insufflation pressure reaching the downloaded insufflation pressure parameter. The console application may provide a graphical and/or audible warning prior to reaching the volume or pressure parameter based on a predetermined warning notification parameter to notify the operator in advance that the insufflation is about to be reached.

At 218, the console application prompts the operator to begin a scout scan and invokes scanning in response to an operator input indicating that the system should now perform a scout scan. The operator can view the imaging data from the scout scan to determine whether the colon is suitably or sufficiently insufflated. In another instance, the quality of insufflation is automatically determined by a computer system based on the scout scan. If the colon is not suitably or sufficiently insufflated (e.g., it collapsed) or if the quality does not satisfy a predetermined threshold quality, then the colon can be further insufflated and validated through another scout scan or otherwise. Otherwise, act 220 is performed.

At 220, the console application invokes the system to scan the colon in response to an operator input indicating the colon should now be scanned. If a second colon scan with the patient in another position (e.g., prone position where the first scan the patient was in the supine position) is to be performed, acts 210 to 220 are repeated for the second position.

At 222, the computing device 122 processes and presents imaging data and insufflation information as described herein. For example, and as noted herein, this may include concurrently or separately presenting imaging data and insufflation information in separate viewing regions or concurrently presenting imaging data and insufflation information in a same viewing region. A user may use the insufflation information to facilitate interpreting the imaging data, including determining whether the insufflation parameter were sufficient for the imaging procedure.

Figure 3:
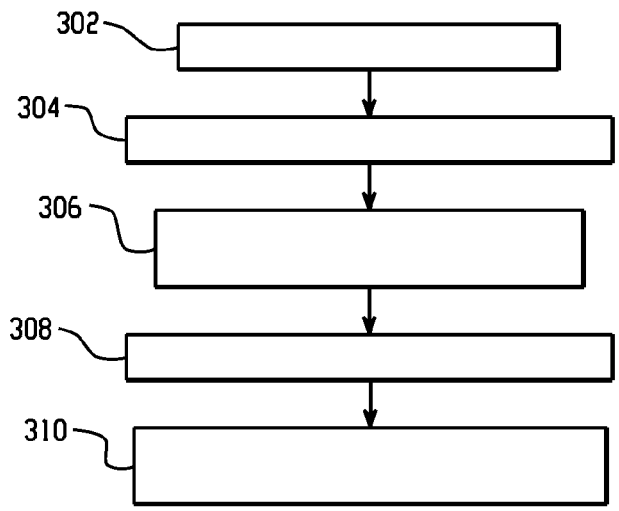
FIG. 3 illustrates a method for validating a colonography imaging procedure.

FIG. 3 illustrate a method for validating a colonography imaging procedure.

At 302, a colonography imaging procedure is performed as described in FIG. 2.

At 304, the computing device 122 obtains insufflation parameters from the imaging protocol.

At 306, the computing device 122 obtains insufflation values from the feedback information provided by the insufflator 120.

At 308, the computing device 122 compares the insufflation parameters with the insufflation values and generates a signal indicative of the comparison.

At 310, the computing device 122 validates the imaging procedure based on the signal. For example, if the insufflation volume value falls within a predetermined acceptable range around the insufflation volume parameter, then the computing device validates the imaging procedure. The computing device 122 generates data indicative of whether the imaging procedure has been validated. The data can be visually and/or audibly presented and/or otherwise used to indicate that the imaging procedure has or has not been validated.

Figure 4:
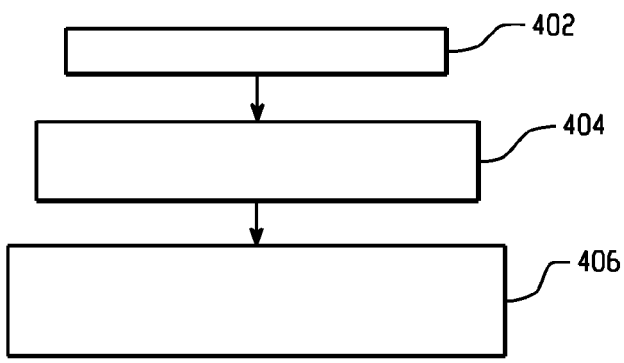
FIG. 4 illustrates a method for generating and/or modifying colonography imaging protocols based on imaging data and/or insufflation information from one or more previously performed colonography procedures.

FIG. 4 illustrate a method for generating and/or modifying colonography imaging protocols.

At 402, a colonography imaging procedure is performed as described in FIG. 2.

At 404, the computing device 122 processes the imaging data and/or the insufflation information.

At 406, the protocol generator 130 generates new and/or modifies imaging protocols based on the processed imaging data and/or insufflation data and user input. As described herein, the protocol generator 130 may use one or more machine-learning algorithms to facilitate generating and/or modifying imaging protocols.

By way of example, this may include modifying insufflation parameters for a subsequent scan where it is determined that the insufflation parameters for an imaging procedure were inadequate, for example, where it is determined that the colon was insufficiently insufflated for a colonography procedure. In another example, this may include generating an imaging protocol for a patient based on a prior scan of another patient.

Figure 5:
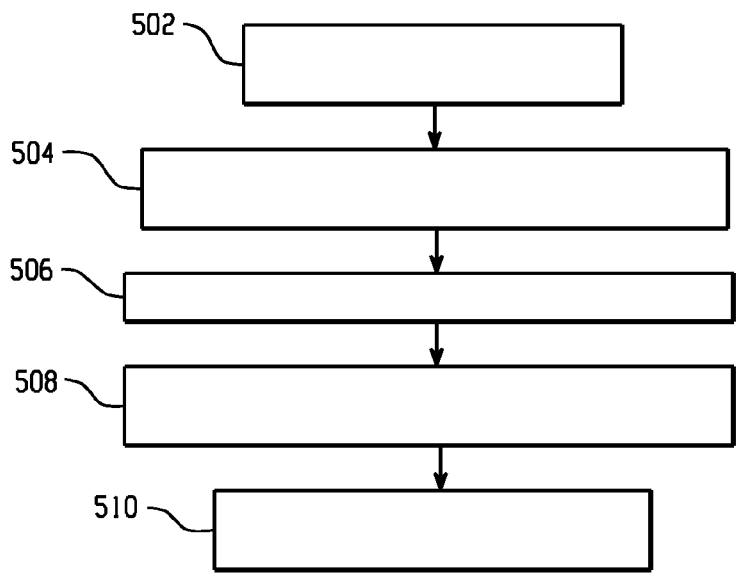
FIG. 5 illustrates a method for generating and/or modifying colonography imaging protocols via a web service.

FIG. 5 illustrate a method for using a web service to generate colonography imaging protocols.

At 502, one or more colonography imaging procedures are performed as described in FIG. 2 or otherwise At 504, the imaging protocols, the resulting imaging data and insufflation parameters, and/or other information is uploaded to the web service 132.

At 506, the web service 132 process the imaging protocols, the resulting imaging data and insufflation parameters, and/or other information, such as information for a patient who will undergo a colonography procedure, user input, etc.

At 508, the web service 132 generates an imaging protocol for the patient based on the uploaded information.

At 510, the generated imaging protocol is downloaded and stored in the protocol bank 116 for use by the system 100.

The above can be implemented as a console application of a scanner and/or an image processing or planning workstation. By way of example, the above may be implemented by way of computer readable instructions, which when executed by a computer processor(s) (a processor of the console 118 or workstation), cause the processor(s) to carry out the described acts. In such a case, the instructions are stored in a computer readable storage medium associated with or otherwise accessible to the relevant computer. In another embodiment, the above can be implemented as a thin-client application such as a portal.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A system, comprising:
an insufflator including:
an insufflation tube configured to insert into a cavity of a subject, wherein the insufflator is configured to blow a gas, via the insufflation tube, into the cavity of the subject, which expands the cavity;
a computed tomography (CT) imaging system including:
a radiation source configured to emit radiation that traverses an examination region; and
a detector array configured to detect radiation traversing the examination region and generate a signal indicative thereof;
a protocol bank configured to store an imaging protocol; and
a console, wherein the console and the insufflator are in communication, the console sets one or more insufflation parameters of the insufflator and the CT imaging system based on the image protocol, and the console controls an operation of the insufflator based on the one or more insufflation parameters.

2. The system of claim 1, wherein the console invokes at least one of the insufflator to begin insufflating and the insufflator to terminate insufflating.

3. The system of claim 1, wherein the one or more insufflation parameters includes at least one of an insufflation volume parameter or an insufflation pressure parameter.

4. The system of claim 1, wherein the insufflator provides insufflation feedback to the console, and the feedback includes at least one of an insufflation volume or an insufflation pressure.

5. The system of claim 1, further comprising a correlator that correlates imaging data received from the imaging system and insufflation information received from the insufflator.

6. The system of claim 5, wherein the correlator correlates the imaging data and the insufflation information based on time.

7. The system of claim 1, further comprising a validator that validates a colonography imaging procedure based on insufflation information received from the insufflator and insufflation parameters from a corresponding imaging protocol.

8. The system of claim 1, further comprising a validator that validates a colonography imaging procedure based on imaging data received from the imaging system, insufflation information received from the insufflator, and user input.

9. The system of claim 1, further comprising a protocol generator that generates a colonography imaging protocol, including one or more insufflation parameters therefore based on one or more insufflation parameters of at least one previously performed colonography imaging procedure.

10. A method, comprising:
controlling an insufflator during a colonography imaging procedure in which the insufflator is used to insufflate the colon of a patient via a console of a computed tomography (CT) imaging system used to perform the colonography imaging procedure,
wherein the insufflator includes an insufflation tube configured to insert into the colon and the console controls the insufflator to blow a gas, via the insufflation tube, into the colon to expand the colon,
wherein CT imaging systems include a radiation source configured to emit radiation that traverses an examination region and a detector array configured to detect radiation traversing the examination region and generate a signal indicative thereof, and
wherein the console sets one or more insufflation parameters of the insufflator and the CT imaging system based on an imaging protocol, and the console controls an operation of the insufflator based on the one or more insufflation parameters.

11. The method of claim 10, further comprising invoking the insufflator to at least one of insufflate or stop insufflating via the console.

12. The method of claim 10, further comprising receiving, at the console, insufflation feedback from the insufflator, including at least one of an insufflation volume or an insufflation pressure.

13. The method of claim 12, further comprising: automatically determining a quality value of the insufflation by the console based on the insufflation feedback.

14. The method of claim 13, further comprising: performing a prescan of the colon, and determining the quality of the insufflation based on the prescan.

15. The method of claim 13, further comprising: prompting an operator of the imaging system to begin the imaging procedure in response to the quality value satisfying a quality threshold.

16. The method of claim 13, further comprising: prompting an operator of the imaging system to further insufflate the colon in response to the quality value failing to satisfy a quality threshold.

17. The method of claim 10, further comprising correlating imaging data received from the imaging system and insufflation information received from the insufflator.

18. The method of claim 17, further comprising correlating imaging data received from the imaging system and insufflation information received from the insufflator.

19. The method of claim 10, further comprising validating the colonography imaging procedure based on insufflation information received from the insufflator and insufflation parameters from a corresponding imaging protocol.

20. The method of claim 10, further comprising validating the colonography imaging procedure based on imaging data received from the imaging system, insufflation information received from the insufflator, and user input.

21. The method of claim 10, further comprising generating a colonography imaging protocol, including one or more insufflation parameters therefore, based on one or more insufflation parameters of at least one previously performed colonography imaging procedure.

22. A method, comprising:
validating, via a processor, a colonography imaging procedure based on insufflation information received from an insufflator controlled by a computed tomography (CT) imaging system and insufflation parameters from a corresponding imaging protocol of the CT imaging system,
wherein the insufflator includes an insufflation tube configured to insert into the cavity and the console controls the insufflator to blow a gas, via the insufflation tube, into the cavity to expand the cavity,
wherein CT imaging systems include a radiation source configured to emit radiation that traverses an examination region and a detector array configured to detect radiation traversing the examination region and generate a signal indicative thereof, and wherein the console sets the insufflation parameters of the insufflator and one or more parameter of the CT imaging system based on the corresponding imaging protocol, and the console controls an operation of the insufflator based on the insufflation parameter.

23. The method of claim 22, further comprising receiving, at the imaging system, insufflation feedback from the insufflator, including at least one of an insufflation volume or an insufflation pressure.

24. A method, comprising:
    generating, via a processor, a colonography imaging protocol, including one or more insufflation parameters for an insufflator controlled by a computed tomography (CT) imaging system executing the imaging protocol, based on one or more insufflation parameters of at least one previously performed colonography imaging procedure,
    wherein the insufflator includes an insufflation tube configured to insert into the cavity and the console controls the insufflator to blow a gas, via the insufflation tube, into the cavity to expand the cavity,
    wherein CT imaging systems include a radiation source configured to emit radiation that traverses an examination region and a detector array configured to detect radiation traversing the examination region and generate a signal indicative thereof, and
    wherein the console configures one or more insufflation parameters of the insufflator and the CT imaging system based on the generating colonography imaging protocol, and the console controls an operation of the insufflator based on the one or more insufflation parameters.

25. The method of claim 24, further comprising receiving, at the imaging system, insufflation feedback from the insufflator, including at least one of an insufflation volume or an insufflation pressure.

26. The method of claim 24, further comprising validating a colonography imaging procedure based on insufflation information received from an insufflator controlled by an imaging system and insufflation parameters from a corresponding imaging protocol.

* * * * *